United States Patent [19]

Gavello

[11] Patent Number: Plant 5,861

[45] Date of Patent: Jan. 20, 1987

[54] HEBE PLANT NAMED LAVENDER LACE

[75] Inventor: Louis E. Gavello, Richmond, Calif.

[73] Assignee: Naka Nurseries, Inc., Fremont, Calif.

[21] Appl. No.: 712,624

[22] Filed: Mar. 18, 1985

[51] Int. Cl.[4] ..... A01H 5/00

[52] U.S. Cl. ..... Plt./54

[58] Field of Search ..... Plt./54

*Primary Examiner*—Robert E. Bagwill

*Attorney, Agent, or Firm*—Flehr, Hohbach, Test, Albritton & Herbert

[57] ABSTRACT

A new and distinct variety of Hebe (Veronica) characterized by floret color conversion from Campanula blue to white.

2 Drawing Figures

1

My invention relates to a new and distinct variety of Hebe (Veronica) plant.

This new and distinct variety, named "Lavender Lace", was discovered by me as a newly found seedling in my nursery at Richmond, Calif. during 1978. The parentage is unknown. However, it is probably a chance seedling of Hebe (Veronica) "Nu-Loe", U.S. Plant Pat. No. 3,493, as the new variety was discovered growing amongst approximately 1000 "Nu-Loe" seedlings.

The plant was asexually propagated by cuttings in 1980 as performed by me at my nursery.

An outstanding characteristic of the new variety is the change in floret color with time. Florets generally blossom first near the bottom of a raceme. Initially, these florets are Campanula Blue as compared with Plate 42:J-10 on pages 106–107 of Directory of Color, 2nd Ed., 1950 by Maerz and Paul. Within several months, usually about two, the floret undergoes a color conversion wherein the floret loses the blue color and becomes white.

Figure 1:
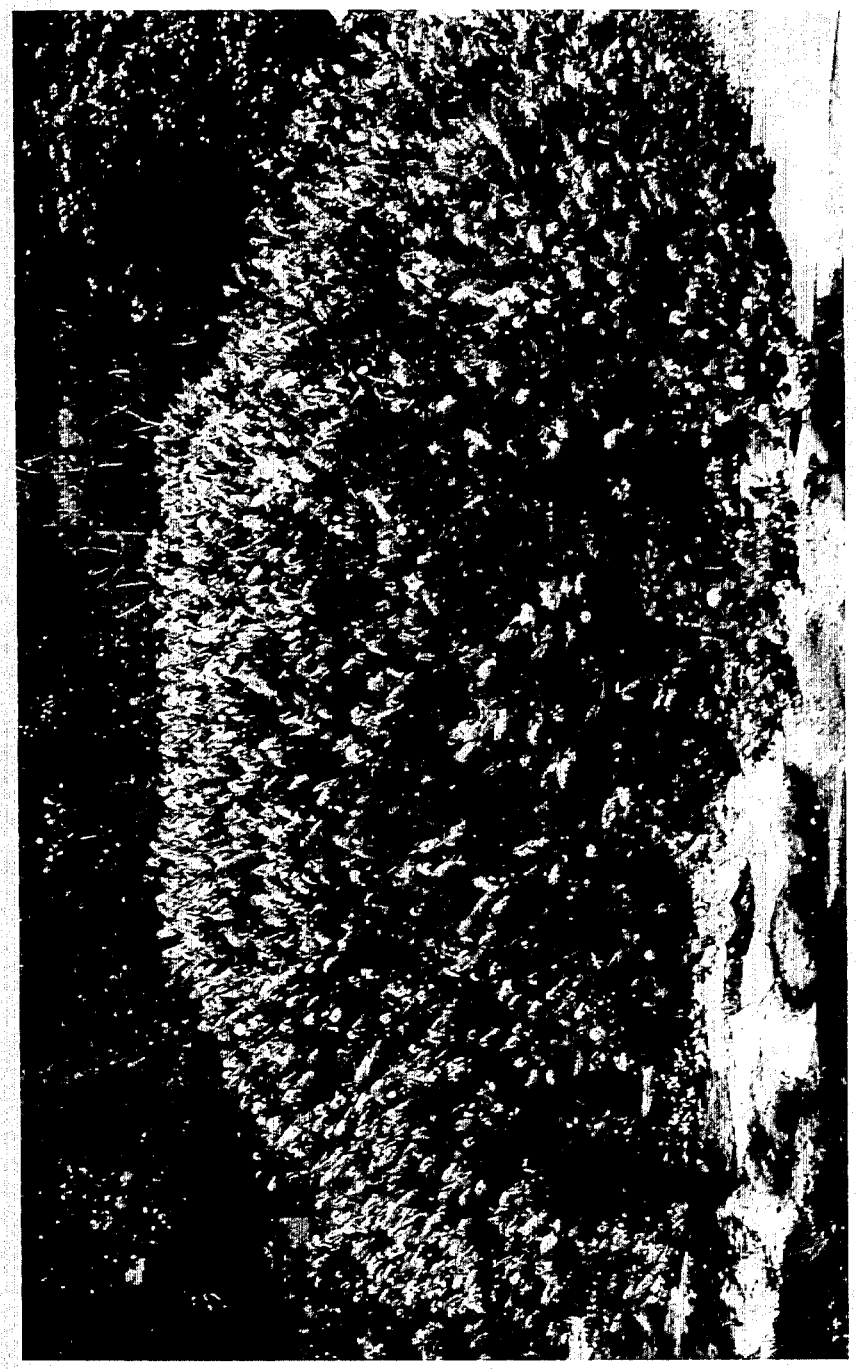
Figure 2:
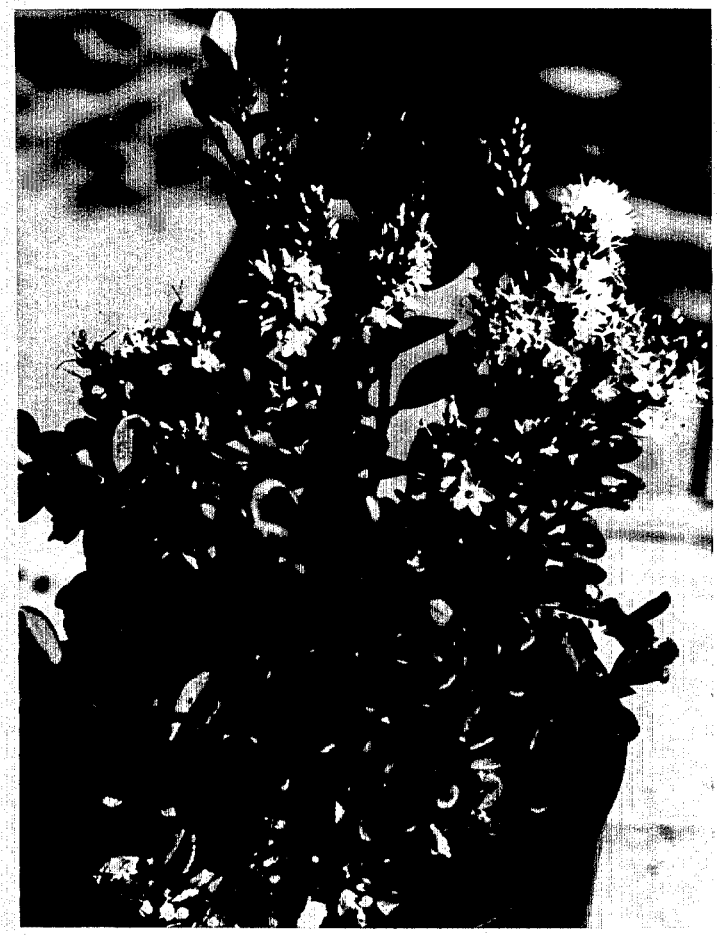

Later blossoming florets higher on the raceme also undergo this color change. If the rate of floret blossoming is high compared to the time required for color conversion, a given raceme may contain florets which initially are all Campanula Blue and which subsequently convert to white as depicted in FIG. 1. If, the blossoming rate is low, a given raceme may simultaneously contain florets which are Campanula Blue and white as shown in FIG. 2. The blossoming rate of florets appears to be lowered when the plant is shaded from direct sunlight.

The accompanying drawings show in FIG. 1 the newly discovered variety of this invention and in FIG. 2 an asexually propagated cutting from the originally discovered new variety.

The following is a detailed description of the new variety, with color terminology in accordance with Maerz and Paul, A Dictionary of Color, 2nd Ed., 1950.

Parentage: Newly found seedling, probably from Hebe (Veronica) "Nu-Loe", U.S. Plant Pat. No. 3,493.

Classification:

*Botanic.*—Hebe (Veronica).

Propagation: Holds its distinguishing characteristics through succeeding propagations by cuttings.

Locality where grown and observed: Richmond, Calif.

Form:

*Bush.*—Prostrate, approximately 12 inches to 16 inches tall, compact, with an approximately 6 foot spread; vigorous and very robust with thick foliage.

2

Rate of growth: 2½ foot spread in 2 years from ground planting.

Time to maturity: 3 to 3½ years.

Branches: Main branches approximately 3 feet; side laterals vary from approximately 2 feet at base of plant to small laterals at tip of main branch; some laterals are located opposite each other and others alternate; many side branches grow from laterals.

*Color.*—Cordovan (Woodland Brown), Plate 8: H-8.

Foliage:

*Leaves.*—Evergreen; glabrous; thick; sessile; obovate, but less obovate than Veronica "Nu-Loe".

*Length of leaves.*—Approximately ⅞ to 1½ inches.

*Width of leaves.*—Approximately ¼ to ¾ inches at widest portion.

*Rib.*—Prominent mid-rib on reverse side, full length of leaf.

*Leaf arrangement.*—Opposite in pairs; decussate, spaced ¼ to ⅞ inches apart.

*Color.*—Fir Green, Plate 24: L-8.

Flower:

*Blooms.*—Reaches full bloom in August in Richmond, Calif.; some flowers and color for most of the year around; repeat.

*Racemes.*—Single on a peduncle; compact, axillary compound; conical elongated; approximately 6 at end of each branch when bush is in full bloom, each approximately 2½ to 3½ inches long and ¾ to 1 inch wide at the base.

*Buds.*—Compact; vary in size from base to tip; each bud is on a small stem (pedicel). Color unopened — green, Plate 20: I-6.

*Florets.*—Four lobed corollas stalked on short peduncle; approximately 40 to 50 florets to each raceme; initially Campanula Blue, Plate 42: J-10, with subsequent color conversion to white.

Weather resistance: Coastal areas of of California;

*Exposure to sun.*—Not recommended.

*Exposure to wind.*—Some.

Disease resistance: Very disease resistant.

Other characteristics: Will grow in most types of soil.

Having described and illustrated my new variety of Hebe (Veronica) plant, I claim:

1. A new and distinct variety of Hebe (Veronica) plant substantially as illustrated and described, characterized as to novelty by floret color conversion from Campanula blue to white.

* * * * *